(12) United States Patent
Nacson

(10) Patent No.: US 8,220,312 B2
(45) Date of Patent: Jul. 17, 2012

(54) NON-INVASIVE METHOD AND SYSTEM FOR SCREENING THE CONTENT OF CONTAINERS FOR THE PRESENCE OF THREAT SUBSTANCES

(75) Inventor: Sabatino Nacson, Toronto (CA)

(73) Assignee: Teknoscan Systems, Inc., Vaughan (CA)

( * ) Notice: Subject to any disclaimer, the term of this patent is extended or adjusted under 35 U.S.C. 154(b) by 129 days.

(21) Appl. No.: 12/791,344

(22) Filed: Jun. 1, 2010

(65) Prior Publication Data

US 2010/0326216 A1 Dec. 30, 2010

Related U.S. Application Data

(60) Provisional application No. 61/219,042, filed on Jun. 22, 2009.

(51) Int. Cl.
*G01N 1/24* (2006.01)
(52) U.S. Cl. .............. 73/31.01; 73/31.02; 73/31.03; 422/88
(58) Field of Classification Search ........... 73/28.01, 73/28.05, 31.01, 31.02, 31.03; 422/88
See application file for complete search history.

(56) References Cited

U.S. PATENT DOCUMENTS

| 4,580,440 | A | | 4/1986 | Reid et al. |
|---|---|---|---|---|
| 4,718,268 | A | | 1/1988 | Reid et al. |
| 4,759,210 | A | * | 7/1988 | Wohltjen ............... 73/31.07 |
| 4,909,090 | A | | 3/1990 | McGown et al. |
| 5,395,589 | A | | 3/1995 | Nacson |
| 5,425,263 | A | | 6/1995 | Davies et al. |
| 5,476,794 | A | | 12/1995 | O'Brien et al. |
| 5,741,984 | A | | 4/1998 | Danylewych-May et al. |
| 5,859,362 | A | | 1/1999 | Neudorfl et al. |
| 5,988,002 | A | | 11/1999 | Danylewych-May et al. |
| 6,707,381 | B1 | * | 3/2004 | Maloney ................ 340/568.1 |
| RE38,797 | E | | 9/2005 | Linker et al. |
| 7,100,424 | B2 | | 9/2006 | Wilson |
| 7,188,513 | B2 | | 3/2007 | Wilson |
| 7,253,413 | B2 | * | 8/2007 | Sauer et al. .............. 250/339.13 |
| 7,456,393 | B2 | | 11/2008 | Napoli |
| 7,468,672 | B2 | | 12/2008 | Harden et al. |
| 2004/0035187 | A1 | * | 2/2004 | Allen et al. ................. 73/31.03 |
| 2007/0266771 | A1 | | 11/2007 | Goldson et al. |
| 2008/0165362 | A1 | * | 7/2008 | Aikaterinidis ............... 356/427 |

FOREIGN PATENT DOCUMENTS

| CA | 2129594 | | 2/1996 |
|---|---|---|---|
| WO | WO 99/38015 | * | 7/1999 |

* cited by examiner

Primary Examiner — Daniel Larkin
(74) Attorney, Agent, or Firm — Kagan Binder, PLLC

(57) ABSTRACT

The invention is a method and system of screening the content of an enclosure, such as a cargo container, for the presence of one or more target substances, such as explosives or drugs, comprising drawing air from the enclosure and passing the drawn air across at least one sampling card having a coating configured to absorb/adsorb the one or more target substances and thereafter analyzing the sampling card to determine if the coating has absorbed/adsorbed one or more target substances. The system embodiment includes a vacuum source, a conduit coupled to the vacuum source and a sampling card holder disposed along the conduit. The sampling card holder removably holds at least one sampling card having a coating thereon configured to absorb/adsorb the one or more target substances, so that air drawn into the conduit from the enclosure passes across the at least one sampling card.

19 Claims, 4 Drawing Sheets

NON-INVASIVE METHOD AND SYSTEM FOR SCREENING THE CONTENT OF CONTAINERS FOR THE PRESENCE OF THREAT SUBSTANCES

PRIORITY

The present non-provisional patent application claims benefit from U.S. Provisional Patent Application Ser. No. 61/219,042, filed on Jun. 22, 2009, by Sabatino Nacson and titled NON-INVASIVE METHOD AND SYSTEM FOR SCREENING THE CONTENT OF CONTAINERS FOR THE PRESENCE OF THREAT SUBSTANCES, wherein the entirety of said provisional patent application is incorporated herein by reference.

FIELD OF THE INVENTION

The present invention relates generally to container content screening and in particular, to a non-invasive method and system for screening the content of containers for the presence of threat substances.

BACKGROUND OF THE INVENTION

Screening freight cargo containers and the like to detect the presence of threat substances or contraband such as for example narcotics, chemical warfare agents, biological warfare agents, nuclear or radiological agents, ammunitions, toxic industrial chemicals or waste, embargoed or smuggled items such as tobacco, human and/or animal stowaways etc. is common practice. To screen freight screen cargo containers, x-ray imaging systems have commonly been employed to scan the content of such containers and generate images that can be examined to determine if any threat substances exist therein. Unfortunately these imaging systems suffer disadvantages in that they are bulky, expensive and require a skillful operator to interpret the generated images in order to distinguish between non-threat substances such as coffee, sugars, flours, rice shipments etc. and threat substances. Even with a skilled operator, high false alarm rates are common. Also, the use of x-rays to image the content of the freight cargo containers can be damaging to the freight cargo container content and may pose potential hazard to the operators.

Other non-imaging techniques to screen the content of freight cargo containers have been considered. One such non-imaging screening technique involves the use of nuclear probing beams, such as thermal neutron, pulsed neutron, accelerated fast neutron or gamma-ray beams to probe freight cargo containers for the existence of threat substances. The interaction of the probing beams with objects inside the freight cargo containers produces secondary gamma-rays, which are detected by suitable arrays of detectors allowing the nature of the freight cargo container content to be determined. Nuclear quadrupole resonance (NQR) has also been employed to scan freight cargo containers and determine the chemical composition of the freight cargo container content. Unfortunately, these non-imaging screening techniques have low detection limits, are unable to detect the amounts of threat substances in freight cargo containers and suffer inaccuracies due to interference from common non-threat substances. These non-imaging screening techniques also require large, complex and expensive installations and screen freight cargo containers at relatively slow rates.

Other screening techniques have also been considered. For example, U.S. Pat. No. 5,859,362 to Neudorfl et al. discloses a method and device for the detection of vapors of cocaine and associated compounds. The method involves sampling a volume of air suspected of containing cocaine vapors, passing the air through a filtration system that removes any particulate matter and binds vapors of cocaine and associated compounds, if present, for further analysis. A preferred associated compound-vapor is that of ecgonidine methyl ester (EDME), and a marker for the presence of cocaine. The device is comprised of sampling, filtration and vacuum port components that can be attached to a container and a suction source, for the sampling of air.

Canadian Patent No. 2,129,594 to Nacson discloses a device for collecting vapors from particulates of target substances for analysis, in an environment which contains considerable extraneous particulates of greater or less volatility than the particulates of target substances. The device comprises a first metal screen surface for collecting the particulates of the target substances in the environment containing the extraneous particulates; heater means connected to the first metal screen surface for maintaining the first metal screen surface at a sufficiently high temperature to volatilize the particulates of the target substances, but not the less volatile extraneous particulates, thereby creating volatized vapors from the target particulates; and a second metal surface for collecting the volatilized vapors from the target particulates for further analysis.

U.S. Pat. No. 5,395,589 to Nacson discloses an apparatus for preconcentrating trace amounts of organic vapors in a sample of air for subsequent detection. The apparatus comprises a metallic substrate, a thin film of fullerenes deposited on the metallic substrate for adsorbing the organic vapors on the thin film of fullerenes, thereby preconcentrating the organic vapors and an apparatus for heating the metallic substrate to a predetermined optimum temperature for desorbing the vapors from the thin film of fullerenes to form desorbed organic vapors for subsequent detection.

U.S. Pat. No. 7,468,672 to Harden et al. discloses a chemical analysis method for detecting, identifying and reporting contraband, illegal drugs, explosives, toxic chemicals, decaying animal and vegetable matter, and concealed human beings located in secure spaces such as cargo shipping containers. Chemical analysis results are accumulated and added to effect definitive analyses over extended periods of time while the containers are in transit. Individual containers are equipped with a device employing the method. The analysis method consists of accumulation and addition of analytical chemical instrumentation, measurements of trace quantities of target chemical vapors inside of shipping containers while the containers are in transit. Cumulative and additive spectrometric analyses coupled with increased target chemical concentrations, due to chemical vapor build up over the long periods of time that containers are in transit, result in significantly increased electronic signal-to-noise in spectrometric measurements and increased spectrometric signal strengths that are indicative of the presence of target chemicals.

U.S. Pat. No. 7,456,393 to Napoli discloses a device for testing surfaces of a card for the presence of explosives, drugs or other substances of interest. The device includes a slot for receiving the card. Thin metallic wiper blades are disposed in alignment with the slot and wipe over surfaces of the card as the card is passed through the slot. Thus, substances on the surface of the card are transferred to the wiper blade. The wiper blade then is enclosed and rapidly heated to desorb the material retrieved from the card. The enclosure then is placed in communication with a detector to test for the presence of substances of interest.

U.S. Pat. Nos. 7,188,513 and 7,100,424 to Wilson disclose systems, methods and apparatus for detecting concealed security threats by sampling molecules of substances for assessment. Inspection of cargo containers by sampling the air contained therein and then analyzing the sampled air from the container for security threats including chemical, biological, radiological, nuclear, and high-explosive threats is permitted without requiring the modification of the existing container, the movement of the container to a particular inspection site, and without opening the container. Nuclear security threats may also be scanned for with close proximity nuclear radiation detection sensors closely coupled to areas at or near the concealed security threats. In addition, detection of other types of contraband, including illegal substances, embargoed materials and human and/or animal stowaways may also be assessed. The concealed security threat detection system generally includes a detection system comprising a detector array, an air-moving device, and one or more air-sampling devices. The system may be mounted upon a vehicle for mobility, run on tracks, cables and pulleys, telescoping and swiveling arms, etc.

U.S. Reissue Pat. No. RE38,797 to Linker et al. discloses an apparatus and method for preconcentrating particles and vapors. The preconcentrator apparatus permits detection of highly diluted amounts of particles in a main gas stream, such as a stream of ambient air. The main gas stream having airborne particles entrained therein is passed through a pervious screen. The particles accumulate upon the screen, as the screen acts as a selective particle filter. The flow of the main gas stream is then interrupted by diaphragm shutter valves, whereupon a cross-flow carrier gas stream is blown parallel past the faces of the screen to dislodge the accumulated particles and carry them to a particle or vapor detector, such as an ion mobility spectrometer. The screen may be heated, such as by passing an electrical current therethrough, to promote desorption of particles therefrom during the flow of the carrier gas.

U.S. Pat. No. 5,988,002 to Danylewych-May et al. discloses a hand held sampling method carried out using an apparatus have a handle, a head connected to the handle and a mechanism for retaining a substrate on the head. The substrate is preferably a sheet-form flexible substrate which is mounted so as to present a collection portion thereof for collection of a sample. The substrate is preferably of a dimension so as to be readily fitted into the inlet portion of an analyzer. The apparatus is manipulated so that the collection portion of the substrate traverses surfaces of interest. The substrate is then removed and placed at the inlet of the analyzer for desorption of a sample. The apparatus enables an area to be sampled quickly and efficiently, while keeping a user's hands away from the surface.

U.S. Pat. No. 5,741,984 to Danylewych-May et al. discloses an apparatus for the collection of a chemical sample from the fingers of an individual for subsequent analytical analysis comprising a token having a base and a substrate on the base. The substrate defines an area such that when the token is removed from a token dispenser the fingers of the individual come into contact with the substrate. Sufficient force must be applied by the fingers of the individual to the substrate when the token is removed from the token dispenser that a chemical sample is transferred from the fingers of the individual to the substrate. The token is then presented for analysis. The substrate may be polytetrafluoroethylene or cotton. A token handler for use in association with the token and an analyzer are also disclosed.

U.S. Pat. Nos. 4,580,440 and 4,718,268 to Reid et al. disclose a method of detecting contraband substances in freight cargo containers in which the container is agitated to disturb particulates therein, and air containing such particulates is then sampled and the particulates collected. The collected particulates include naturally occurring particulates which have absorbed vapors of the contraband substance during the entire time that the container has been closed, and also include particulates of the contraband substance itself. The collected particulates are then heated to a temperature above 160° C. to drive off vapors indicative of the contraband substance and the vapors are analyzed in a mass analyzer.

Many techniques have also been developed for screening passengers and their luggage. For example, U.S. Pat. No. 4,909,090 to McGown et al. discloses a portable, hand-held vapor sampling probe for collecting vapors of compounds such as cocaine, heroin, and explosives prior to their desorption and analysis in a vapor detector. Rechargeable batteries power a lamp in the front face of the probe for heating target portions of a sampling surface, a puffer assembly for directing air jets at the target, and a motor for drawing air samples through a collector coil on whose surfaces vapors are trapped. A flexible U-shaped shroud on the front face partially encloses the lamp and collector and helps to regulate air flow over the target and to protect the probe from damage. Upon contact with a surface, the shroud may activate a switch which, together with a second switch on the probe handle and a lamp pyrometer, regulates heating of the target.

U.S. Pat. No. 5,425,263 to Davies et al. discloses an assembly for preferentially separating and collecting particles that are gathered from the surface of an article such as an item of baggage. The assembly features an impactor and a suction anvil that is displaceable from a collection medium. The anvil is displaceable from the collection medium so that the medium may be removed and analyzed for traces of substances such as explosives or narcotics. There is also provided, in combination with the assembly, a vacuum head and conduit for gathering the particles and a suction unit for creating the suction force. The collection medium containing collected particles is moved from the impactor to an analyzer by a stage movement device. The analyzer includes an analysis unit, such as an ion mobility spectrometer, and a displaceable heater anvil.

U.S. Pat. No. 5,476,794 to O'Brien et al. discloses a method of rapidly checking surfaces for the presence of traces of specific compounds such as certain explosives and drugs. A hand-covering such as a cotton glove is used to wipe surfaces to pick up particles of the specific compound which may indicate the presence of larger amounts or previous contact of a surface by a person who has handled the compound. The particles are transferred, unheated, to collection surfaces of a hand-held sample probe by vacuuming of the gloved hand by the battery-operated probe. Heat is then supplied by a source external to the probe to vaporize the particles, and the vapors are analyzed by a suitable technique such as high speed gas chromatography.

U.S. Patent Application Publication No. 2007/0266771 to Goldson et al. discloses a capture system to enable volatiles associated with targeted materials located within a confined environment to be trapped over a period of time to enable the volatiles to be concentrated. The capture system comprises a package having a "surface" which is constructed in a manner that it can be located within a confined environment to trap specific volatiles associated with the targeted materials. The captured volatiles are desorbed from the surface and are analysed and the results compared with known signature volatile profiles from the targeted materials.

Although various techniques for detecting the presence of threat substances are described above, improvements are continually being sought. It is therefore an object of the present invention to provide a novel non-invasive method and system for screening the content of containers for the presence of threat substances.

SUMMARY OF THE INVENTION

Accordingly, in one aspect there is provided a method of screening the content of an enclosure for the presence of one or more target substances comprising drawing air from the enclosure and passing the drawn air across at least one sampling card having a coating configured to absorb/adsorb the one or more target substances and thereafter analyzing the sampling card to determine if the coating has absorbed/adsorbed one or more target substances.

According to another aspect there is provided a system for screening the content of an enclosure for the presence of one or more target substances comprising a vacuum source, a conduit coupled to the vacuum source and a sampling card holder disposed along the conduit. The sampling card holder removably holds at least one sampling card having a coating thereon configured to absorb/adsorb the one or more target substances, so that air drawn into the conduit from the enclosure passes across the at least one sampling card.

BRIEF DESCRIPTION OF THE DRAWINGS

Embodiments will now be described more fully with reference to the accompanying drawings in which.

DETAILED DESCRIPTION OF THE EMBODIMENTS

Figure 1:
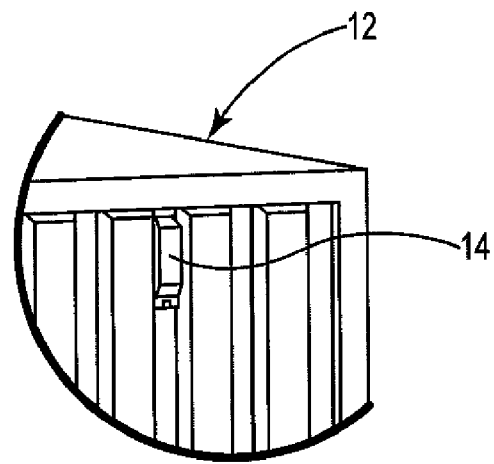
FIG. 1 shows a portion of a freight cargo container including an air vent.
Figure 2A:
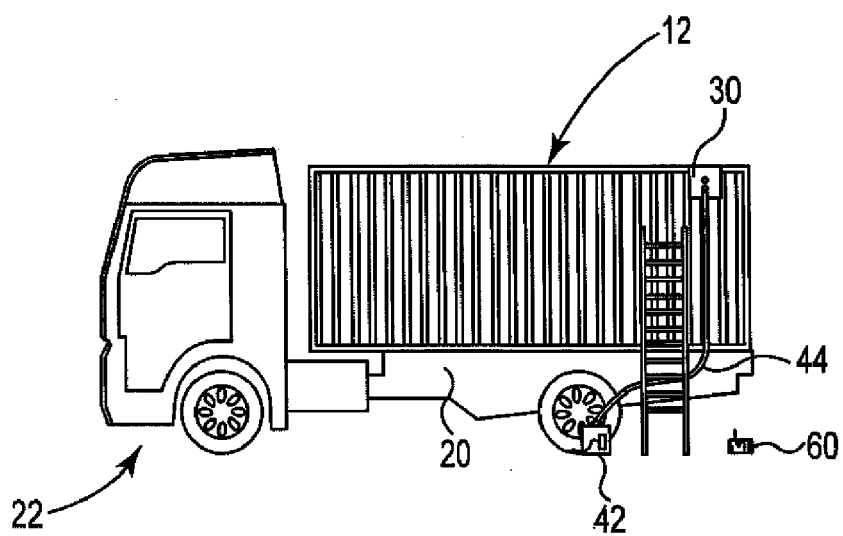
FIG. 2a shows a freight cargo container supported on the bed of a truck being screened for the presence of threat substances.
Figure 2B:
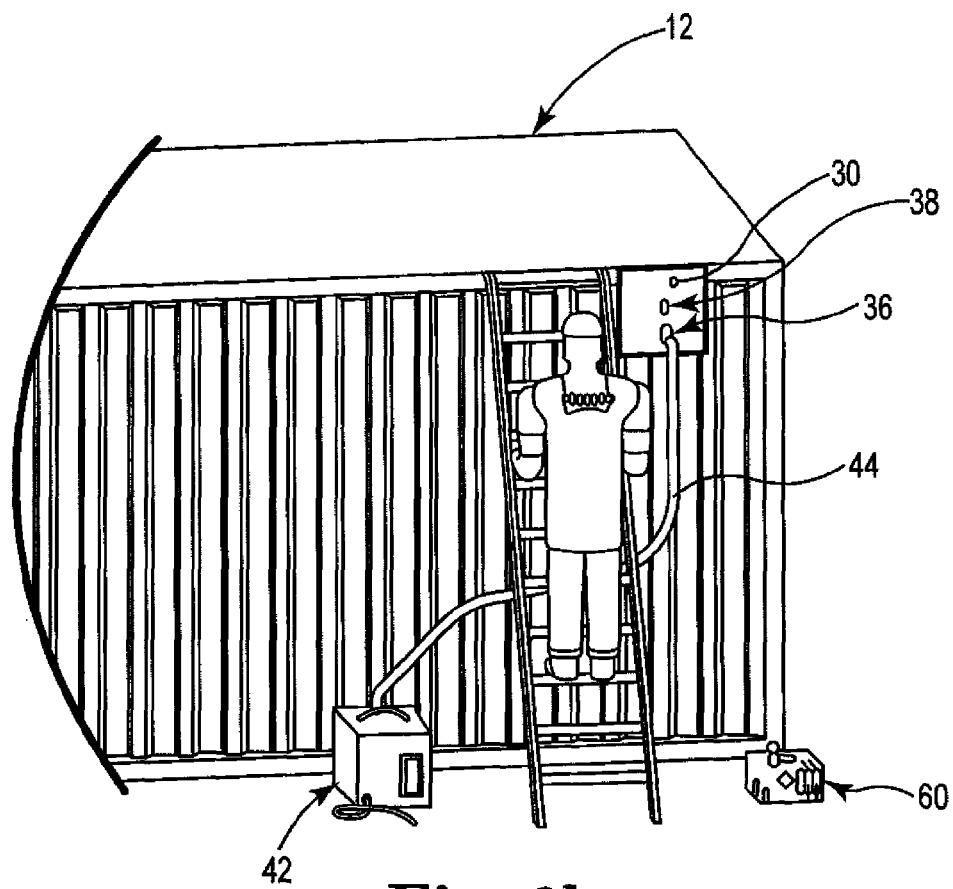
FIG. 2b shows a sea or rail freight cargo container being screened for the presence of threat substances.

It is well established that residues from explosive materials are abundant on surfaces after handling explosive materials, and are difficult to remove. Similarly, volatile explosives, such as TATP, HMTD, EGDN, DMNB, NG, DNT and TNT are readily detected due to the fact that these explosives evaporate into the surrounding air even when concealed. Consequently, direct sampling of air from within an enclosure, such as for example freight cargo containers, provides a very reliable method of detecting threat substances such as explosive materials that may be concealed in such enclosures. The same applies to other threat substances such as those referred to in the background section of the subject application.

In the following, a method and system for screening freight cargo containers and the like by sampling the air within the freight cargo containers to remove vapors and airborne particles from inside the freight cargo containers and entrapping such vapors and airborne particles on a treated card for subsequent analysis without the need to open the freight cargo containers are described.

Turning now to FIGS. 1 to 4, a freight cargo container 12 comprising an air vent 14 that is to be screened for the presence of threat substances is shown. FIG. 2a shows the freight cargo container 12 supported on the bed 20 of a truck 22. FIG. 2b shows the freight cargo container 12 unsupported. In order to sample air from within the freight cargo container 12 in order to screen the content of the freight cargo container to detect the presence of threat substances therein, a screening system is provided. In this embodiment, the screening system comprises a stainless steel plate 30 that is magnetically secured to the side of the freight cargo container 12 over the air vent 14. The steel plate 30 forms a seal with the freight cargo container 12 and has an outlet port 32 configured to receive the inlet port 34 of a sampling card holder 36. Sampling card holder 36 has a slot in its upper surface that removably receives a sampling card 38. The outlet port 40 of the sampling card holder 36 is connected to a high volume vacuum sampler unit 42 through a heavy duty hose 44.

Figure 4:
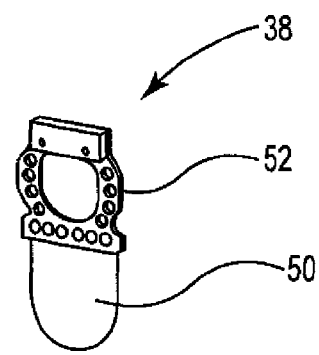
FIG. 4 shows a sampling card on which threat substances are accumulated during screening of a freight cargo container.
Figure 3:
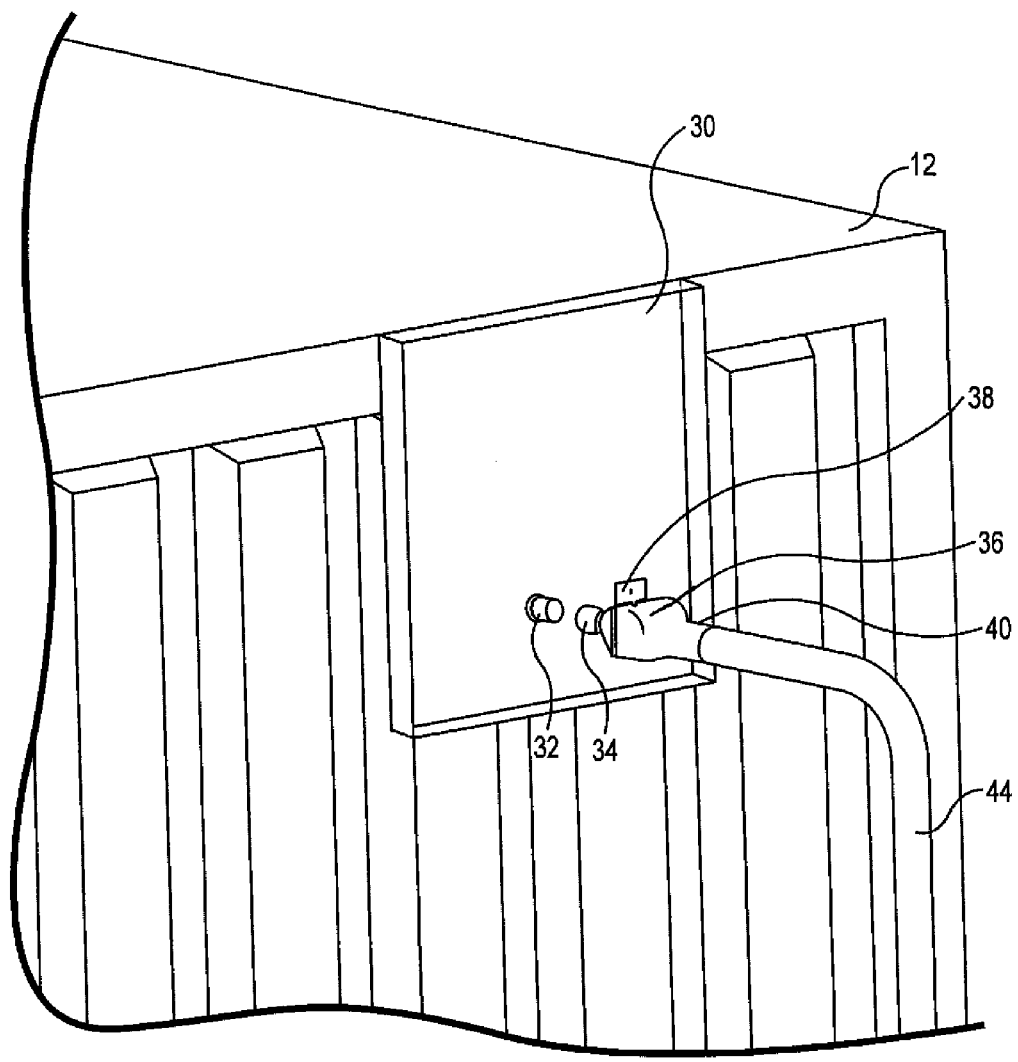
FIG. 3 shows an enlarged portion of the freight cargo containers of FIGS. 2a and 2b.

FIG. 4 best illustrates the sampling card 38. As can be seen, the sampling card 38 comprises a substrate 50 coated with a combination of adsorbent/absorbent materials designed to concentrate vapors and entrap fine airborne particles of threat substances for subsequent thermal desorption and analysis. A handle 52 is formed at one end of the substrate 50 to facilitate handling of the sampling card 38 allowing the sampling card to be readily inserted into and removed from the slot of the sampling card holder 36. As is best shown in FIG. 3, when the sampling card 38 is inserted into the sampling card holder 36, the substrate 50 presents a major surface facing the outlet port 32 thereby to ensure good air flow across the substrate 50.

In this embodiment, the substrate 50 is formed of a stainless steel mesh. Other substrate materials can of course be used such as for example, nickel, copper, aluminum, fiberglass, porous Teflon, cotton, Nomex and other man-made fibers.

In this embodiment, the combination of adsorbent/absorbent materials comprises two or more of diphenylene oxide polymer(s) prepared in chloroform, carbon composite materials such as graphite, fullerenes, polymeric carbons from soot produced from nitro substituted alkylbenzenes, divinyl benzene, mono-alkyl substituted benzenes, di-alkyl substituted benzene, toluene, xylenes, ethylbenzene, silicone oils with high thermal stability and boiling points and adsorption properties for wide range of organic compounds or other suitable materials.

During operation, when it is desired to screen a freight cargo container 12 for threat substances, a sampling card 38 is inserted into the slot of the sampling card holder 36 and the vacuum sampler unit 42 is turned on for a sampling interval selected to suit the size and configuration of the freight cargo container being sampled. Typically the sampling interval is in the range of from about 2 to about 5 minutes. The vacuum sampler unit 42 once turned on draws air out of the freight cargo container 12 via the air vent 14 at a high rate generally equal to about 1,300 liters/min. This high volume sampling rate has been found to provide relatively strong air movement inside the cargo freight container 12. The air exiting the freight cargo container 12 via the air vent 14 enters the sampling card holder 36 via the ports 32 and 34. Air entering the sampling card holder 36 passes across the coated substrate 50 of the sampling card 38 held thereby before entering the hose 44 via the outlet port 40.

As the air that is drawn from the freight cargo container 12 passes across the coated substrate 50 of the sampling card 38, localized vapors and airborne particles within the air are entrapped by the adsorbent/absorbent materials coating the substrate 50 of the sampling card 38.

When the sampling interval expires, the vacuum sampler unit 42 shuts off. The sampling card 38 is then manually removed from the slot of the sampling card holder 36 via the handle 52 and is transported to an analyzer 60 at the site of the freight cargo container 12. The analyzer 60 in turn heats the sampling card 38 to evaporate entrapped vapors and release entrapped particles and rapidly analyses the vapors and particles (e.g. 10-30 seconds) to detect the presence of threat substances. The analyzer 60 may for example be a chromatographic analyzer, a mass spectrometer (stationary or portable), chemiluminescent detector, an axial ion mobility spectrometer (IMS), a field assymetric ion mobility spectrometry (FAIMS) and a differential mobility spectrometer (DMS).

Upon completion of the sampling card analysis, the freight cargo container 12 is electronically tagged if a positive indication of the presence of a threat substance is encountered. During tagging a coded radio transmitter (+/−100 Hz or other suitable frequency) is attached to the freight cargo container 12 in a hidden or inconspicuous location, allowing the tagged freight cargo container 12 to be tracked. As will be appreciated, typically in a port or terminal, freight cargo containers are constantly moved from one location to another until cleared to leave the port or terminal. Tracking freight cargo containers identified as containing threat substances throughout their movement at the port or terminal helps to ensure that such freight cargo containers are located and more closely examined. Freight cargo containers that are identified as containing threat substances can also be x-ray imaged to detect for non-chemical threats such as for example firearms, weapons, etc.

Figure 5:
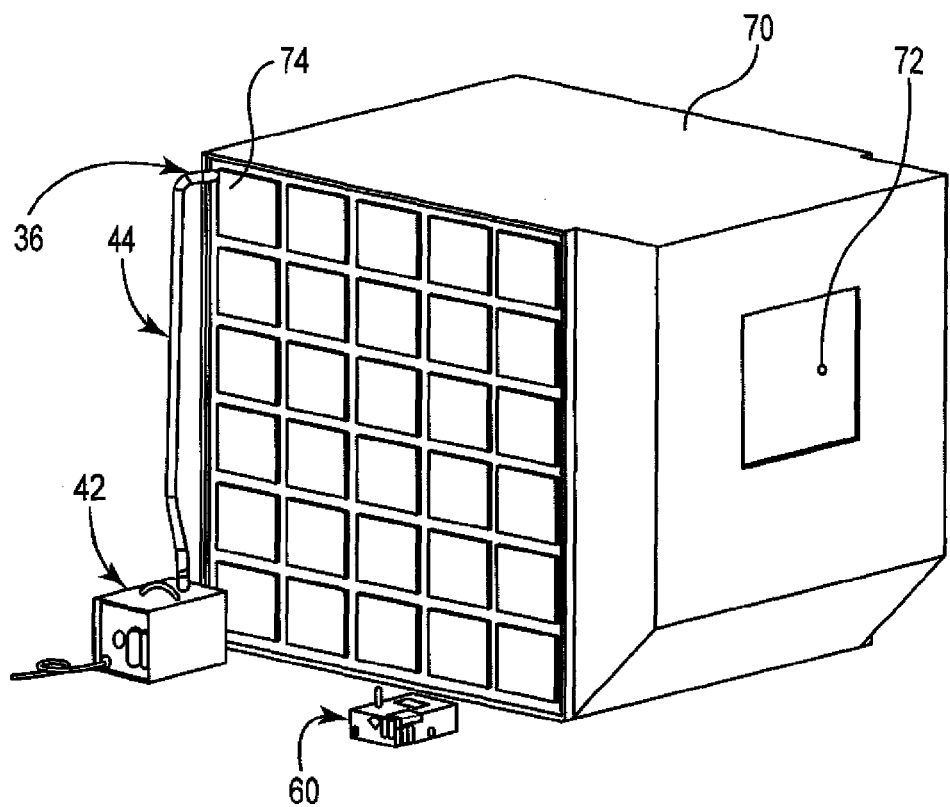
FIG. 5 shows of an air freight cargo container being screened for the presence of threat substances.

FIG. 5 shows the screening system used to sample air from within an air freight cargo container 70. In this case, the sampling card holder 36 that is fitted onto one end of the hose 44 is inserted into the air freight cargo container 70 either via a flapper door 72 provided at one end of the air freight cargo container or via a door 74 provided in a side of the air freight cargo container 70.

Research indicates that the expected concentration of threat substances inside freight cargo containers is likely to be in the parts per trillion levels and that the size of airborne particles of threat substance is likely to be in the range of from about 1 to about 150 micrometers. Given these expected concentration levels and particle sizes, in order to ensure that freight cargo containers are adequately screened for the presence of threat substances, a high volume sampling rate sufficient to ensure good air flow within the freight cargo containers is required. As mentioned above, a high volume sampling rate of about 1,300 liters/min has been found to be acceptable. The sampling interval that is selected during screening is a function of the internal volume of the freight cargo container being screened.

For example, the internal volumes of a conventional 20 foot sea freight cargo container and a conventional 40 foot sea freight cargo container are approximately 33.1 m³ and 67.5 m³, respectively. Table 1 below shows the percentage volume of air sampled from various empty freight cargo containers during different sampling intervals at a high volume sampling rate of about 1,300 liters/min.

TABLE 1

| Sampling interval min | 20' sea freight cargo container | 40' sea freight cargo container | LD-4 air freight cargo container | LD-7 air freight cargo container |
|---|---|---|---|---|
| 2 | 8% | 4% | 52% | 25% |
| 5 | 20% | 10% | >100% | 62% |
| 10 | 39% | 20% | >100% | >100% |
| 15 | 59% | 30% | >100% | >100% |

Consider that air is drawn from a freight cargo container at a sampling rate, $Q_s$ in m³/min, and that a threat substance is present in the freight cargo container at a concentration, $C_s$ in ng/L. If a sample of the threat substance is collected by the sampling card 38 with a trapping efficiency $E_T$ during a sampling interval $t_s$ in minutes, the amount of threat substance collected by the sampling card 38 in nanograms can be expressed as:

$$N_s = E_T \times Q_s \times C_s \times t_s \quad \text{Equation 1}$$

If the trapped sample of threat substance on the sampling card 38 is heated to evaporate the trapped sample into a desorption carrier gas flow in the analyzer 60 traveling at a flow rate, $Q_d$, then the concentration of desorbed target threat compound $C_d$ can be expressed as:

$$C_d = N_s / Q_d \times t_d \quad \text{Equation 2}$$

where $t_d$ is desorption time in minutes

Desorption temperature and flow rate govern the desorption profile of the threat substance of interest and can be tailored to accommodate different types of analyzer data acquisition and ionization sources.

The enrichment factor for volatile threat substances in the freight cargo container is defined by combining Equations 1 and 2:

$$E_F = E_T \times Q_s \times t_s / Q_d \times t_d \quad \text{Equation 3}$$

Typically, for a high volume sample acquisition, $Q_s = 1.3$ m³/min and $t_s$ is variable from 2 minutes to 15 minutes, normally 2 minutes for air freight cargo containers and 5 to 10 minutes for sea freight cargo containers. Assuming for example, $t_s = 2$ minutes, $Q_d = 0.5$ L/min, time $t_d = 20$ seconds, and $E_T = 0.5$, according to Equation 3, the enrichment factor is:

$$E_F = 0.5 \times 1,300 \times 2 / 0.5 \times 0.3$$
$$= 8,666$$

The typical detection limit of an IMS or MS system is around 100 picogram for some explosives. As will therefore be appreciated, even at extremely low concentrations in the order of parts per trillion, explosives can be detected. The corresponding $C_s$ concentration in a sampled air freight cargo container is:

$$C_8 = 100 \, pg / 0.5 \times 1,300 \times 2 \, \text{min}$$
$$= 0.077 \, pg/L \text{ or for } TNT \text{ vapor concentration } 0.0083 \, ppt \text{ at}$$
$$\text{standard temperature and pressure } (STP) \text{ conditions}$$

Experimental results with a TNT vapor generator, with diluted concentration when sampled with the high volume vacuum system were estimated at 10 pptv. Sampling was carried out for 30 seconds and the resulting data are shown in Table 2 below for seven consecutive runs on the vapor generator.

TABLE 2

| Run # | Detector Signal | Equivalent amount | TNT concentration pptv |
|---|---|---|---|
| 1 | 139 pA | 1.0 ng | 0.22 |
| 2 | 163 | 1.1 | 0.24 |

TABLE 2-continued

| Run # | Detector Signal | Equivalent amount | TNT concentration pptv |
|---|---|---|---|
| 3 | 120 | 0.8 | 0.18 |
| 4 | 146 | 1.0 | 0.22 |
| 5 | 156 | 1.1 | 0.24 |
| 6 | 137 | 0.9 | 0.18 |
| 7 | 176 | 1.2 | 0.26 |

TNT vapors were concentrated and held in the coating of the sampling card 38 and were not lost during sample collection under extreme flow rates. As can be seen, low TNT vapor concentration were collected and detected.

Volatile explosives will be manifested at elevated vapor concentrations in the headspace of the cargo freight containers, whereas, particle detection will involve collection of nano to micro meters particle sizes of sufficient density to produce high signals in the high nanogram levels at the analyzer end.

While the method and screening system have been described with primary reference to detecting the presence of threat substances within enclosures, such as for example freight cargo containers, those of skill in the art will appreciate that the method and system may be employed in other environments. For example, the method and system may be used for sampling airborne particles and vapors in the HVAC ventilation system of a pharmaceutical factory, where the permitted airborne particle concentration is one nanogram per liter for drugs such as antibiotics, steroids, hormones and pharmaceutical drugs. Of course, the method and system may be employed in virtually any environment where it is desired to sample air to detect the presence of target substances.

Although the sampling card holder 36 is shown as including a single slot, those of skill in the art will appreciate that the sampling card holder may comprise multiple slots allowing each slot to hold a sampling card with a different substrate coating configured to absorb/adsorb different threat substances.

Although particular examples of analyzers are described above, those of skill in the art will appreciate that other suitable analyzers may be used. Those of skill in the art will also appreciate that some analytical techniques will be more efficient or preferred than others by virtue of various operational features, such as size, field deployment, need for inert carrier gases and susceptibility to potential chemical interferences that would normally be encountered in sampling complex chemical matrices found usually found cargo container environments.

Although embodiments have been described above with reference to the drawings, those of skill in the art will appreciate that variations and modifications may be made without departing from the spirit and scope thereof as defined by the appended claims.

What is claimed is:

1. A method of screening the content of an enclosure for the presence of one or more target substances, the method comprising:
    drawing air from the enclosure and passing the drawn air across at least one sampling card having a coating configured to absorb/adsorb the one or more target substances, the coating comprising at least two different materials, each material comprising one of diphenylene oxide polymers prepared in chloroform, divinyl benzene or a carbon composite material; and
    thereafter analyzing the card to determine if the coating has absorbed/adsorbed one or more target substances.

2. The method of claim 1 wherein the coating comprises diphenylene oxide polymers prepared in chloroform.

3. The method of claim 1 wherein the coating comprises divinyl benzene.

4. The method of claim 1 wherein the coating comprises a carbon composite material comprising graphite.

5. The method of claim 1 wherein the coating comprises a carbon composite material comprising fullerenes.

6. The method of claim 1 wherein the coating comprises a carbon composite material comprising polymeric carbons from soot produced from nitro substituted alkylbenzene.

7. The method of claim 1 wherein the coating comprises a carbon composite material comprising polymeric carbons from soot produced from mono-alkyl substituted benzenes.

8. The method of claim 1 wherein the coating comprises a carbon composite material comprising polymeric carbons from soot produced from di-alkyl substituted benzene.

9. The method of claim 1 wherein the coating comprises a carbon composite material comprising polymeric carbons from soot produced from toluene.

10. The method of claim 1 wherein the coating comprises a carbon composite material comprising polymeric carbons from soot produced from xylenes.

11. The method of claim 1 wherein the coating comprises a carbon composite material comprising polymeric carbons from soot produced from ethylbenzene.

12. The method of claim 1 wherein the coating comprises at least three different materials, each material comprising diphenylene oxide polymers prepared in chloroform, divinyl benzene, or a carbon composite material.

13. The method of claim 1 wherein the coating comprises at least four different materials, each material comprising diphenylene oxide polymers prepared in chloroform, divinyl benzene, or a carbon composite material.

14. A system for screening the content of an enclosure for the presence of one or more target substances, the system comprising:
    a vacuum source;
    a conduit coupled to said vacuum source; and
    a sampling card holder disposed along said conduit, said sampling card holder removably holding at least one sampling card having a coating thereon configured to absorb/adsorb the one or more target substances, the coating comprising at least two different materials, each material comprising one of diphenylene oxide polymers prepared in chloroform, divinyl benzene or a carbon composite material, so that air drawn into said conduct from the enclosure passes across the at least one sampling card.

15. The system of claim 14 wherein the coating comprises diphenylene oxide polymers prepared in chloroform.

16. The system of claim 14 wherein the coating comprises divinyl benzene.

17. The system of claim 16 wherein the coating comprises at least four different materials, each material comprising diphenylene oxide polymers prepared in chloroform, divinyl benzene, or a carbon composite material.

18. The system of claim 14 wherein the coating comprises a carbon composite material comprising graphite, fullerenes or one or more polymeric carbons from soot produced from a material selected from the group consisting of nitro substituted alkylbenzenes, mono-alkyl substituted benzenes, di-alkyl substituted benzene, toluene, xylenes, and ethylbenzene.

19. The system of claim 14 wherein the coating comprises at least three different materials, each material comprising diphenylene oxide polymers prepared in chloroform, divinyl benzene, or a carbon composite material.

* * * * *